(12) United States Patent
Song et al.

(10) Patent No.: US 7,939,342 B2
(45) Date of Patent: May 10, 2011

(54) DIAGNOSTIC TEST KITS EMPLOYING AN INTERNAL CALIBRATION SYSTEM

(75) Inventors: Xuedong Song, Roswell, GA (US); Chibueze Obi Chidebelu-Eze, Atlanta, GA (US); Rosann Marie Matthews Kaylor, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 425 days.

(21) Appl. No.: 11/094,498

(22) Filed: Mar. 30, 2005

(65) Prior Publication Data
US 2006/0223193 A1    Oct. 5, 2006

(51) Int. Cl.
*G01N 33/53* (2006.01)

(52) U.S. Cl. ........ 436/514; 436/501; 436/518; 436/523; 436/8; 436/15; 436/975; 435/4; 435/7.1; 435/287.1; 435/287.2; 435/287.8; 435/287.9; 435/288.7; 422/82.05; 422/82.08

(58) Field of Classification Search ............... 422/61, 422/68.1, 82.05, 82.08; 435/4, 7.1, 287.1, 435/287.2, 287.8, 287.9, 288.7; 436/501, 436/518, 523, 8, 15
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,385,126 A | 5/1983 | Chen et al. | |
| 4,442,204 A | 4/1984 | Greenquist et al. | |
| 4,614,723 A | 9/1986 | Schmidt et al. | |
| 4,742,011 A | 5/1988 | Blake et al. | |
| 4,743,560 A | 5/1988 | Campbell et al. | |
| 4,835,099 A | 5/1989 | Mize et al. | |
| 4,889,816 A | 12/1989 | Davis et al. | |
| 4,904,583 A | 2/1990 | Mapes et al. | |
| 4,920,046 A | 4/1990 | McFarland et al. | |
| 4,954,435 A | 9/1990 | Krauth | |
| 4,956,302 A | 9/1990 | Gordon et al. | |
| 4,978,625 A | 12/1990 | Wagner et al. | |
| 4,980,298 A | 12/1990 | Blake et al. | |
| 5,028,535 A | 7/1991 | Buechler et al. | |

(Continued)

FOREIGN PATENT DOCUMENTS

AU          759407 B2      2/2000

(Continued)

OTHER PUBLICATIONS

Article—*A New Tetradentate β-Diketonate-Europium Chelate That Can Be Covalently Bound to Proteins for Time-Resolved Fluoroimmunoassay*, Jingli Yuan et al., Analytical Chemistry, vol. 70, No. 3, Feb. 1, 1998, pp. 596-601.

(Continued)

*Primary Examiner* — Bao-Thuy L Nguyen
(74) *Attorney, Agent, or Firm* — Dority & Manning, P.A.

(57) ABSTRACT

A diagnostic test kit that employs a lateral flow assay device and a plurality of assay reagents for detecting a test analyte within a test sample is disclosed. The assay reagents include detection probes that are capable of producing a detection signal representing the presence or quantity of the test analyte in the test sample. To further enhance detection accuracy, calibration probes are also used that are capable of producing a calibration signal representing the presence or quantity of a calibration analyte. The calibration signal may be utilized to calibrate the detection signal.

23 Claims, 4 Drawing Sheets

U.S. PATENT DOCUMENTS

| | | |
|---|---|---|
| 5,047,044 A | 9/1991 | Smith et al. |
| 5,073,340 A | 12/1991 | Covington et al. |
| 5,075,077 A | 12/1991 | Durley, III et al. |
| 5,075,078 A | 12/1991 | Osikowicz et al. |
| 5,089,391 A | 2/1992 | Buechler et al. |
| 5,120,643 A | 6/1992 | Ching et al. |
| 5,149,622 A | 9/1992 | Brown et al. |
| 5,185,127 A | 2/1993 | Vonk |
| 5,208,143 A | 5/1993 | Henderson et al. |
| 5,252,459 A | 10/1993 | Tarcha et al. |
| 5,275,785 A | 1/1994 | May et al. |
| 5,387,503 A | 2/1995 | Selmer et al. |
| 5,395,754 A | 3/1995 | Lambotte et al. |
| 5,428,690 A | 6/1995 | Bacus et al. |
| 5,464,741 A | 11/1995 | Hendrix |
| 5,518,883 A | 5/1996 | Soini |
| 5,573,909 A | 11/1996 | Singer et al. |
| 5,573,919 A | 11/1996 | Kearns et al. |
| 5,585,279 A | 12/1996 | Davidson |
| 5,591,581 A | 1/1997 | Massey et al. |
| 5,591,645 A | 1/1997 | Rosenstein |
| 5,602,040 A | 2/1997 | May et al. |
| 5,610,077 A | 3/1997 | Davis et al. |
| 5,622,871 A | 4/1997 | May et al. |
| 5,637,509 A | 6/1997 | Hammila et al. |
| 5,656,503 A | 8/1997 | May et al. |
| 5,670,381 A | 9/1997 | Jou et al. |
| 5,714,389 A | 2/1998 | Charlton et al. |
| 5,731,147 A | 3/1998 | Bard et al. |
| 5,788,863 A | 8/1998 | Milunic |
| 5,851,776 A | 12/1998 | Valkirs |
| 5,856,203 A | 1/1999 | Robinson et al. |
| 5,922,537 A | 7/1999 | Ewart et al. |
| 5,945,281 A | 8/1999 | Prabhu |
| 5,989,924 A | 11/1999 | Root et al. |
| 5,989,926 A | 11/1999 | Badley et al. |
| 5,998,221 A | 12/1999 | Malick et al. |
| 6,004,530 A | 12/1999 | Sagner et al. |
| 6,030,840 A | 2/2000 | Mullinax et al. |
| 6,077,669 A | 6/2000 | Little et al. |
| 6,103,536 A | 8/2000 | Geisberg |
| 6,121,008 A | 9/2000 | Fitzpatrick et al. |
| 6,130,100 A | 10/2000 | Jobling et al. |
| 6,133,048 A | 10/2000 | Penfold et al. |
| 6,156,271 A | 12/2000 | May |
| 6,187,269 B1 | 2/2001 | Lancesseru et al. |
| 6,194,220 B1 | 2/2001 | Malick et al. |
| 6,274,324 B1 | 8/2001 | Davis et al. |
| 6,294,391 B1 | 9/2001 | Badley et al. |
| 6,352,862 B1 | 3/2002 | Davis et al. |
| 6,399,398 B1 | 6/2002 | Cunningham et al. |
| 6,524,864 B2 | 2/2003 | Fernandez de Castro |
| 6,613,583 B1 | 9/2003 | Richter et al. |
| 6,627,459 B1 * | 9/2003 | Tung et al. ............ 436/514 |
| 6,653,149 B1 | 11/2003 | Tung et al. |
| 6,669,908 B2 | 12/2003 | Weyker et al. |
| RE38,430 E | 2/2004 | Rosenstein |
| 6,846,638 B2 | 1/2005 | Shipwash |
| 6,893,880 B2 | 5/2005 | Carpenter |
| 6,951,631 B1 | 10/2005 | Catt et al. |
| 7,044,919 B1 | 5/2006 | Catt et al. |
| 7,052,831 B2 | 5/2006 | Fletcher et al. |
| 2002/0042149 A1 | 4/2002 | Butlin et al. |
| 2002/0045273 A1 | 4/2002 | Butlin et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2004/0043502 A1 | 3/2004 | Song et al. |
| 2004/0121334 A1 | 6/2004 | Wei et al. |
| 2004/0151632 A1 | 8/2004 | Badley et al. |
| 2004/0161859 A1 | 8/2004 | Guo et al. |
| 2004/0235189 A1 * | 11/2004 | Lu ......................... 436/514 |
| 2004/0241700 A1 | 12/2004 | Lamont et al. |
| 2005/0036148 A1 | 2/2005 | Phelan et al. |
| 2005/0037510 A1 | 2/2005 | Sharrock et al. |
| 2005/0048599 A1 * | 3/2005 | Goldberg et al. ............ 435/34 |
| 2005/0107956 A1 | 5/2005 | Fukunaga et al. |
| 2005/0109951 A1 | 5/2005 | Fish et al. |
| 2005/0112635 A1 | 5/2005 | Gentle et al. |
| 2005/0112779 A1 | 5/2005 | Wei et al. |
| 2005/0112780 A1 | 5/2005 | Song |
| 2006/0003390 A1 | 1/2006 | Schaeffler et al. |
| 2006/0024842 A1 * | 2/2006 | Nylese ..................... 436/514 |
| 2006/0029924 A1 | 2/2006 | Brewster et al. |
| 2006/0246522 A1 | 11/2006 | Bhullar et al. |

FOREIGN PATENT DOCUMENTS

| | | |
|---|---|---|
| EP | 0253464 A1 | 1/1988 |
| EP | 1491892 A1 | 12/2004 |
| WO | WO 97/09620 * | 3/1997 |
| WO | WO 2004034056 A2 | 4/2004 |
| WO | WO 2004034056 A3 | 4/2004 |

OTHER PUBLICATIONS

Article—*One-step all-in-one dry reagent Immunoassays with fluorescent europium chelate label and time-resolved fluorometry*, Timo Lövgren, et al., Clinical Chemistry 42:8, 1996, pp. 1196-1201.

Article—*Production of the Long Pentraxin PTX3 in Advanced Atherosclerotic Plaques*, Rolph et al., Arteriosclerosis Thrombosis and Vascular Biology, 2002, 22, atvb.ahajournals.org.

Search Report and Written Opinion for PCT/US2006/002252, Jun. 29, 2006.

International Search Report for cross referenced file KCX-1050 (20833)—Int'l Application No. PCT/US2006/016756.

* cited by examiner

DIAGNOSTIC TEST KITS EMPLOYING AN INTERNAL CALIBRATION SYSTEM

BACKGROUND OF THE INVENTION

Various analytical procedures and devices are commonly employed in assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

There are several well-known immunoassay methods that use immunoreactants labeled with a detectable component so that the analyte may be detected analytically. For example, "sandwich-type" assay formats typically involve mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described in by U.S. Pat. No. 4,168,146 to Grubb, et al. and U.S. Pat. No. 4,366,241 to Tom, et al. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

Many of these assays rely upon calibration to provide valid and meaningful results, particularly for semi-quantitative and quantitative detections. In external calibration systems, a standard curve is usually obtained from standard samples containing a series of a known amount of analyte, and the results obtained from the samples are then compared with the standard curve to extract the presence and/or amount of the analyte in the sample. The external calibration method is relatively easy to design and simple to implement. However, it is often subject to interference from environmental and batch-to-batch variations, and is thus unreliable.

Some internal calibration systems have thus been developed to overcome these problems. For example, U.S. Pat. No. 5,387,503 to Selmer, et al. describes an internal calibration technique that involves mixing a sample of a known volume with a predetermined amount of a calibrator analyte and contacting the mixture with a solid support. The solid support contains a reagent capable of selectively binding the test analyte in a first discrete area and a reagent capable of selectively binding the calibrator analyte in a second discrete area. A mixture of a labeled reagent for the test analyte and a similarly labeled reagent for the calibrator analyte are also applied to the solid support. The amount of test analyte in the sample is determined by comparing the levels of labeled reagent bound to the test and calibrator analytes, respectively. Unfortunately, such internal calibration techniques are not readily incorporated into lateral flow devices, which involve heterogeneous separation of the analyte using chromatographic methods. In addition, the requirement for pre-mixing the assay reagents is burdensome and overly complicated, particularly for point-of-care applications in which the ultimate user is not a trained medical professional or technician.

As such, a need currently exists for an accurate internal calibration system for lateral flow assays that is accurate, yet relatively inexpensive, simple, and easy to use.

SUMMARY OF THE INVENTION

In accordance with one embodiment of the present invention, a diagnostic test kit is disclosed for detecting the presence or quantity of a test analyte within a test sample. The diagnostic test kit comprises a lateral flow assay device comprising a porous membrane. The porous membrane defines a detection zone and a calibration zone. A first receptive material is immobilized within the detection zone and a second receptive material is immobilized within the calibration zone. Besides the lateral flow assay device, the diagnostic test kit also comprises a plurality of assay reagents, one or more of which are disposed on the lateral flow assay device. The assay reagents comprise a calibration analyte, detection probes, and calibration probes. The detection probes are conjugated with a first specific binding member configured to preferentially bind to the test analyte, the first receptive material, or combinations thereof. The calibration probes are conjugated with a second specific binding member configured to preferentially bind to the calibration analyte, the second receptive material, or combinations thereof.

In accordance with another embodiment of the present invention, a method for quantitatively or semi-quantitatively detecting a test analyte using a lateral flow device is disclosed. The device comprises a porous membrane in communication with detection probes conjugated with a first specific binding member and calibration probes conjugated with a second specific binding member. The porous membrane also defines a detection zone and a calibration zone. The method comprises contacting the lateral flow device with a calibration analyte; contacting the lateral flow device with the test sample; measuring the intensity of a detection signal produced at the detection zone; and measuring the intensity of a calibration signal produced at the calibration zone. The amount of the test analyte is proportional to the intensity of the detection signal as calibrated by the intensity of the calibration signal.

In accordance with still another embodiment of the present invention, a method for quantitatively or semi-quantitatively detecting a test analyte using a lateral flow device is disclosed. The device comprises a porous membrane in communication with a calibration analyte, detection probes conjugated with a first specific binding member, and calibration probes conjugated with a second specific binding member. The porous membrane also defines a detection zone and a calibration zone. The method comprises contacting the lateral flow device with the test sample; measuring the intensity of a detection signal produced at the detection zone; and measuring the intensity of a calibration signal produced at the calibration zone. The amount of the test analyte is proportional to the intensity of the detection signal as calibrated by the intensity of the calibration signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
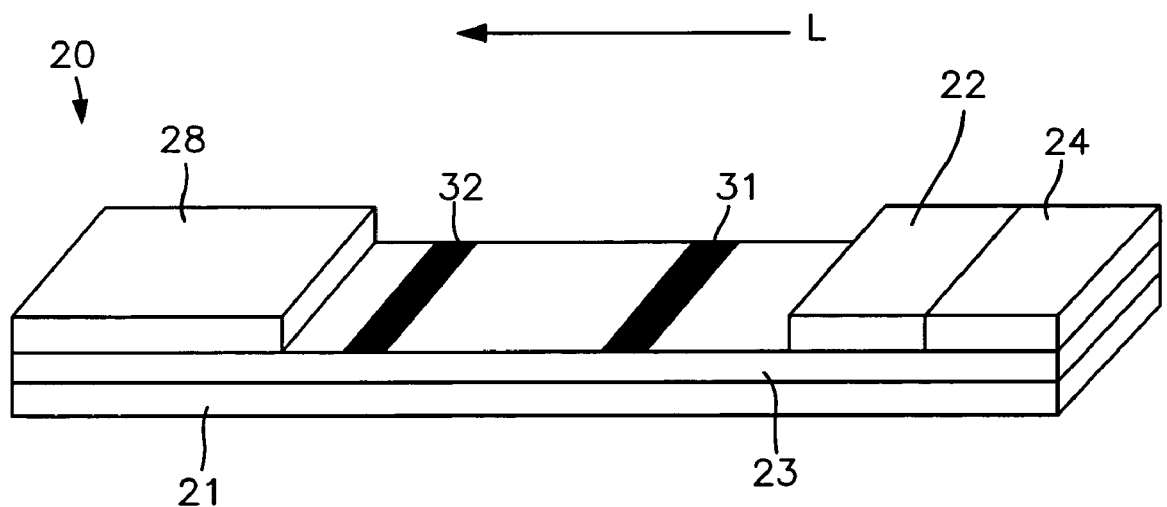
FIG. 1 is a perspective view of one embodiment of a lateral flow assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a diagnostic test kit that employs a lateral flow assay device and a plurality of assay reagents for detecting a test analyte within a test sample. The assay reagents include detection probes that are capable of producing a detection signal representing the presence or quantity of the test analyte in the test sample. To further enhance detection accuracy, calibration probes are also used that are capable of producing a calibration signal representing the presence or quantity of a calibration analyte. The calibration signal may be utilized to calibrate the detection signal.

The calibration analyte is normally either foreign to the test sample or present at a constant concentration so that it is easier to distinguish between the test analyte and calibration analyte. Further, it is also normally desired that the calibration analyte exhibit a similar degradation profile (or loss of activity over time) to the test analyte with respect to conditions of pH, temperature, salt concentration, etc. In this manner, the calibration analyte will behave similarly under the same reaction conditions and storage time so that the calibration curve of the calibration analyte will be substantially similar to the calibration curve of the test analyte. If desired, for example, the calibration analyte may be a member of the same protein family as the test analyte. In one embodiment, the test analyte is C-reactive protein ("CRP"), which is a globulin that forms a precipitate with the somatic C-polysaccharide of the *Strep-*

*tococcus pneumoniae*. CRP belongs to the "pentraxin" family of proteins, which are oligomeric plasma proteins that have a pentagonal cyclic symmetry with five noncovalently bound subunits. There are two common branches of the "pentraxin" family, i.e., "CRP-like" proteins and Serum Amyloid P ("SAP") like proteins. Proteins that bind phosphocholine are considered CRP-like, while proteins that bind carbohydrate moieties are considered SAP-like. Thus, in an embodiment in which CRP is the test analyte, the selected calibration analyte may be a member of the pentraxin family, and even more desirably a pentraxin protein that binds with phosphocholine. Some examples of such phosphocholine-binding pentraxin proteins include, but are not limited to, pentraxin 3 ("PTX3"), neuronal pentraxin 1, and neuronal pentraxin 2. See e.g., *Arteriosclerosis, Thrombosis, and Vascular Biology: Production of the Long Pentraxin PTX3 in Advanced Atherosclerotic Plaques*; Michael S. Rolph, et al.; 2002; 22:e10. However, it is not necessary that the calibration analyte is a member of the same family as the test analyte. In fact, many applications require a lower level of calibration accuracy, and as such, less expensive and more readily available calibration analytes may be employed. In one embodiment, for example, a calibration analyte for CRP may be a protein selected from a non-pentraxin family of proteins (e.g., dimer, trimer, etc.), such as albumin, bovine serum albumin (BSA), β-casein, or hCG, all of which are believed to have a similar degradation profile as CRP.

As stated above, detection and calibration probes are employed in the present invention for detecting the test analyte and calibration analyte, respectively. The calibration probes generally contain the same type of detectable substance as the detection probes. Any substance capable of producing a signal that is detectable visually or by an instrumental device may be used as the detection or calibration probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2,2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2,2'bipyridine)ruthenium (II); (2,2'-bipyridine)[bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, luminescent compounds may have a relatively long emission lifetime and a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (III)). Such chelates may exhibit strongly redshifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-Eu$^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns.

It is generally desired to modify the detection and calibration probes in some manner so that they are more readily able to bind to a respective analyte or receptive material. In such instances, the probes may be modified with certain specific binding members that are adhered thereto to form conjugated probes. Specific binding members generally refer to a member of a specific binding pair, i.e., two different molecules where one of the molecules chemically and/or physically binds to the second molecule. The selection of the specific binding member generally depends on the test analyte of interest and on the corresponding calibration analyte. To ensure independent assay performance, it is normally desired that the detection probes are conjugated with a member of a different specific binding pair than the calibration probes. In this manner, the conjugated calibration probes will preferentially bind with the calibration analyte (sandwich and indirect assay formats) or with a specific binding member for the calibration analyte (competitive assay formats). The conjugated calibration probes will not, however, generally bind with the test analyte or with a specific binding member for the test analyte. As such, assays may be simultaneously performed for the test analyte and the calibration analyte without fear of substantial cross-reaction, thereby allowing the calibration analyte assay to be used in calibrating the test antigen. Also, similar to the relationship between the calibration analyte and the test analyte, it is normally desired that the specific binding members exhibit a similar degradation profile with respect to conditions of pH, temperature, salt concentration, storage time, etc.

Some examples of suitable immunoreactive specific binding members that may be used in the present invention include, but are not limited to, antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art.

Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the probe may contain a relatively high surface concentration of polar groups. In addition, although probes are often functionalized after synthesis, such as with poly (thiophenol), the probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting probes may then be contacted with ethanolamine, for instance, to block any remaining activated sites. Overall, this process forms a conjugated probe, where the antibody is covalently attached to the probe. Besides covalent bonding, other attachment techniques, such as physical adsorption, may also be utilized in the present invention.

Regardless of the manner in which they are formed, the detection probes and calibration probes are typically disposed on the assay device prior to application of the test sample. The pre-application of the probes to the assay device provides a variety of benefits. For example, pre-application eliminates the need for a subsequent user to handle and mix the reagents with the test sample or a diluent. This is particularly useful in point-of-care applications where the user is not generally a trained lab technician or medical professional. In some embodiments, for example, the detection and calibration probes are disposed downstream from the point where the test sample is to be applied. In this manner, the test sample is capable of mixing with and optionally re-suspending the probes upon application. Alternatively, the probes may be positioned upstream from the point of application of the test sample. For instance, a diluent may be employed to re-suspend the probes for performing the assay. Similarly, the calibration analyte may also be disposed on the assay device prior to application of the test sample. Although the particular location may vary, it is generally desired that the calibration analyte is applied upstream from the detection probes and calibration probes. In this manner, the calibration analyte is able to readily mix with the test sample before contacting the calibration probes, thereby enhancing binding therebetween.

The calibration analyte may also be mixed with the test sample prior to application to the assay device. As such, the calibration analyte is subjected to substantially the same conditions as the test analyte prior to performance of the assay. This may further optimize calibration accuracy.

Referring now to FIG. 1, one embodiment of a lateral flow assay device 20 that may be employed in conjunction with the internal calibration system of the present invention will now be described in more detail. As shown, the device 20 contains a porous membrane 23 optionally supported by a rigid material 21. In general, the porous membrane 23 may be made from any of a variety of materials through which the test sample is capable of passing. For example, the materials used to form the porous membrane 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the porous membrane 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the porous membrane 23. For example, the support 21 may be positioned directly adjacent to the porous membrane 23 as shown in FIG. 1, or one or more intervening layers may be positioned between the porous membrane 23 and the support 21. Regardless, the support 21 may generally be formed from any material able to carry the porous membrane 23. The support 21 may be formed from a material that is transmissive to light, such as transparent or optically diffuse (e.g., transluscent) materials. Also, it is generally desired that the support 21 is liquid-impermeable so that fluid flowing through the membrane 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the porous membrane 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the porous membrane 23 may be cast onto the support 21, wherein the resulting laminate may be die-cut to the desired size and shape. Alternatively, the porous membrane 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, III, et al., which is incorporated herein in its entirety by reference thereto for all purposes.

The device 20 may also contain an absorbent pad 28. The absorbent pad 28 generally receives fluid that has migrated through the entire porous membrane 23. As is well known in the art, the absorbent pad 28 may assist in promoting capillary action and fluid flow through the membrane 23.

To initiate the detection of an analyte within the test sample, a user may directly apply the test sample to a portion of the porous membrane 23 through which it may then travel in the direction illustrated by arrow "L" in FIG. 1. Alternatively, the test sample may first be applied to a sample pad 24 that is in fluid communication with the porous membrane 23. Some suitable materials that may be used to form the sample pad 24 include, but are not limited to, nitrocellulose, cellulose, porous polyethylene pads, and glass fiber filter paper. If desired, the sample pad 24 may also contain one or more assay pretreatment reagents, either diffusively or non-diffusively attached thereto. For example, in one embodiment, the calibration analyte may be disposed on the sample pad 24 so that it contacts the test sample upon application thereto.

In the illustrated embodiment, the test sample travels from the sample pad 24 to a conjugate pad 22 that is placed in communication with one end of the sample pad 24. The conjugate pad 22 is formed from a material through which the test sample is capable of passing. For example, in one embodiment, the conjugate pad 22 is formed from glass fibers. Although only one conjugate pad 22 is shown, it should be understood that multiple conjugate pads may also be used in the present invention. In one particular embodiment of the present invention, the detection and calibration probes (not shown) are applied to the conjugate pad 22. After application, the probes are then dried to inhibit migration therefrom. The conjugate pad 22 provides a matrix for the deposition of the probes so that they are free to migrate when rehydrated. More specifically, when a liquid test sample contacts the probes, they are rehydrated and become re-suspended and/or re-solubilized. Of course, it should be understood that the probes may be applied to various other locations of the assay device 20 as well, such as directly to the membrane 23, so long as they are capable of being rehydrated by the test sample upon contact therewith.

Referring again to FIG. 1, the porous membrane 23 also defines various zones configured to perform the assay. For instance, the porous membrane 23 defines a detection zone 31 that contains a first receptive material that is capable of binding to the conjugated detection probes (or complexes thereof) that pass through the length of the membrane 23. The first receptive material is immobilized on the porous membrane 23 and may be selected from the same materials as the specific binding members described above, including, for instance, antigens; haptens; antibody-binding proteins, such as protein A, protein G, or protein A/G; neutravidin (a deglysolated avidin derivative), avidin (a highly cationic 66,000-dalton glycoprotein), streptavidin (a nonglycosylated 52,800-dalton protein), or captavidin (a nitrated avidin derivative); primary or secondary antibodies, and derivatives or fragments thereof. In some embodiments, the first receptive material is an antibody specific to an antigen within the test sample. In sandwich assay formats, for example, the first receptive material may serve as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized first receptive material. Upon being bound to the immobilized receptive material, the complexed probes form a new ternary sandwich complex.

The assay device 20 also includes a calibration zone 32. In this embodiment, the calibration zone 32 is formed on the porous membrane 23 and is positioned downstream from the detection zone 31. Alternatively, however, the calibration zone 32 may also be positioned upstream from the detection zone 31. The calibration zone 32 is provided with a second receptive material that is capable of binding to the conjugated calibration probes (or complexes thereof) that pass through the length of the membrane 23. The second receptive material may be a member of the specific binding pair used for conjugating the calibration probes. In this manner, the second receptive material preferentially binds to the calibration probes (or complexes thereof). For example, when the calibration analyte is an antigen, the second receptive material may be an antibody (e.g., sandwich or competitive assay formats) or an antigen (e.g., indirect assay format). Also, as discussed above, it is normally desired that the first and second receptive materials exhibit a similar degradation profile with respect to conditions of pH, temperature, salt concentration, storage time, etc.

The detection zone 31 and calibration zone 32 may each provide any number of distinct detection regions so that a user may better determine the concentration of the analyte within the test sample. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20.

When it is desired to semi-quantitatively or quantitatively determine the concentration of the analyte within the test sample, the intensity of the detection signal "$I_s$" produced at the detection zone 31 may be compared with the intensity of the calibration signal "$I_c$" produced at the calibration zone 32. For example, in some embodiments (e.g., sandwich assay formats), the quantity of analyte is directly proportional to the ratio of $I_s$ to $I_c$. In other embodiments (e.g., competitive and indirect assay formats), the quantity of analyte in excess of the predefined base quantity is inversely proportional to the ratio of $I_s$ to $I_c$. Based upon the range in which the ratio falls, the general concentration range for the analyte may be determined. If desired, the ratio of $I_s$ to $I_c$ may be plotted versus the analyte concentration for a range of known analyte concentrations to generate a calibration curve. To determine the quantity of analyte in an unknown test sample that is in excess of a predefined base quantity, the signal ratio may then be converted to analyte concentration according to the calibration curve. It should be noted that alternative mathematical relationships between $I_s$ and $I_c$ may be plotted versus the analyte concentration to generate the calibration curve. For example, in one embodiment, the value of $I_s/(I_s+I_c)$ may be plotted versus analyte concentration to generate the calibration curve. Regardless, calibration and sample testing may be conducted under approximately the same conditions at the same time, thus providing reliable quantitative or semi-quantitative results, with increased sensitivity.

If desired, an optical reader may be used in some embodiments to measure the intensity of the probes at the detection zone 31 and/or calibration zone 32. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the presence of probes that exhibit fluorescence. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to detect the presence of detection probes.

Typically, the optical reader contains an illumination source that is capable of emitting electromagnetic radiation and a detector that is capable of registering a signal (e.g., transmitted or reflected light, emitted fluorescence or phosphorescence, etc.). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the assay device. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into a system for use with a membrane-based device. If silicon photodiodes are used, then the wavelength range of the emitted signal may be within their range of sensitivity, which is 400 to 1100 nanometers.

Detection and calibration may be performed automatically and/or manually in accordance with the present invention. For example, a microprocessor may optionally be employed to convert signal intensities from a detector to a result that quantitatively or semi-quantitatively indicates the concentration of the analyte. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used. If desired, the results may be conveyed to a user using a liquid crystal (LCD) or LED display.

Figure 2:
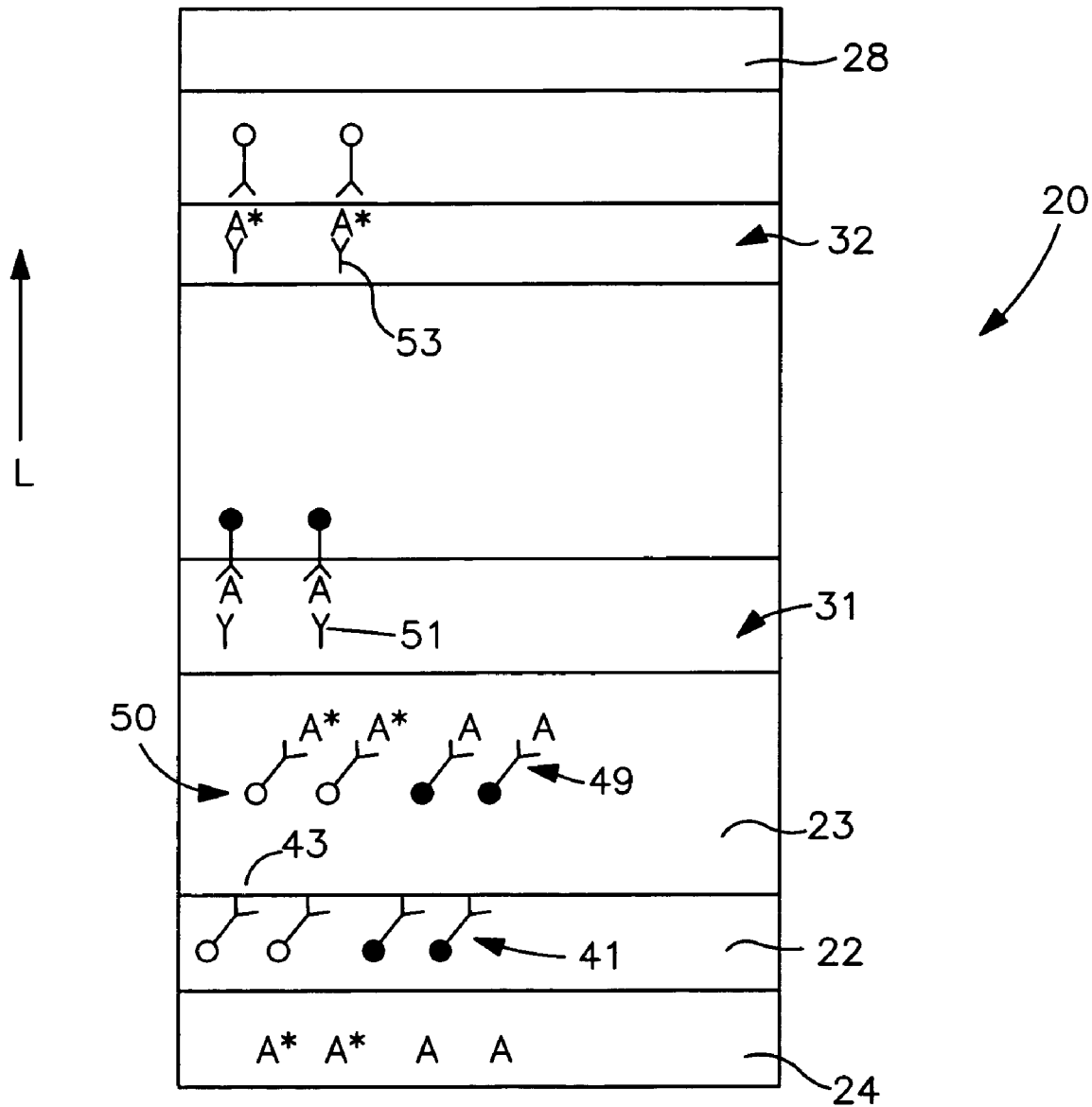
FIG. 2 is a schematic illustration of one embodiment of a sandwich assay format that may be used in accordance with the present invention.

Referring to FIG. 2, one embodiment of a method for detecting the presence of a test antigen A (e.g., CRP) using a sandwich assay format will now be described in more detail.

Figure 3:
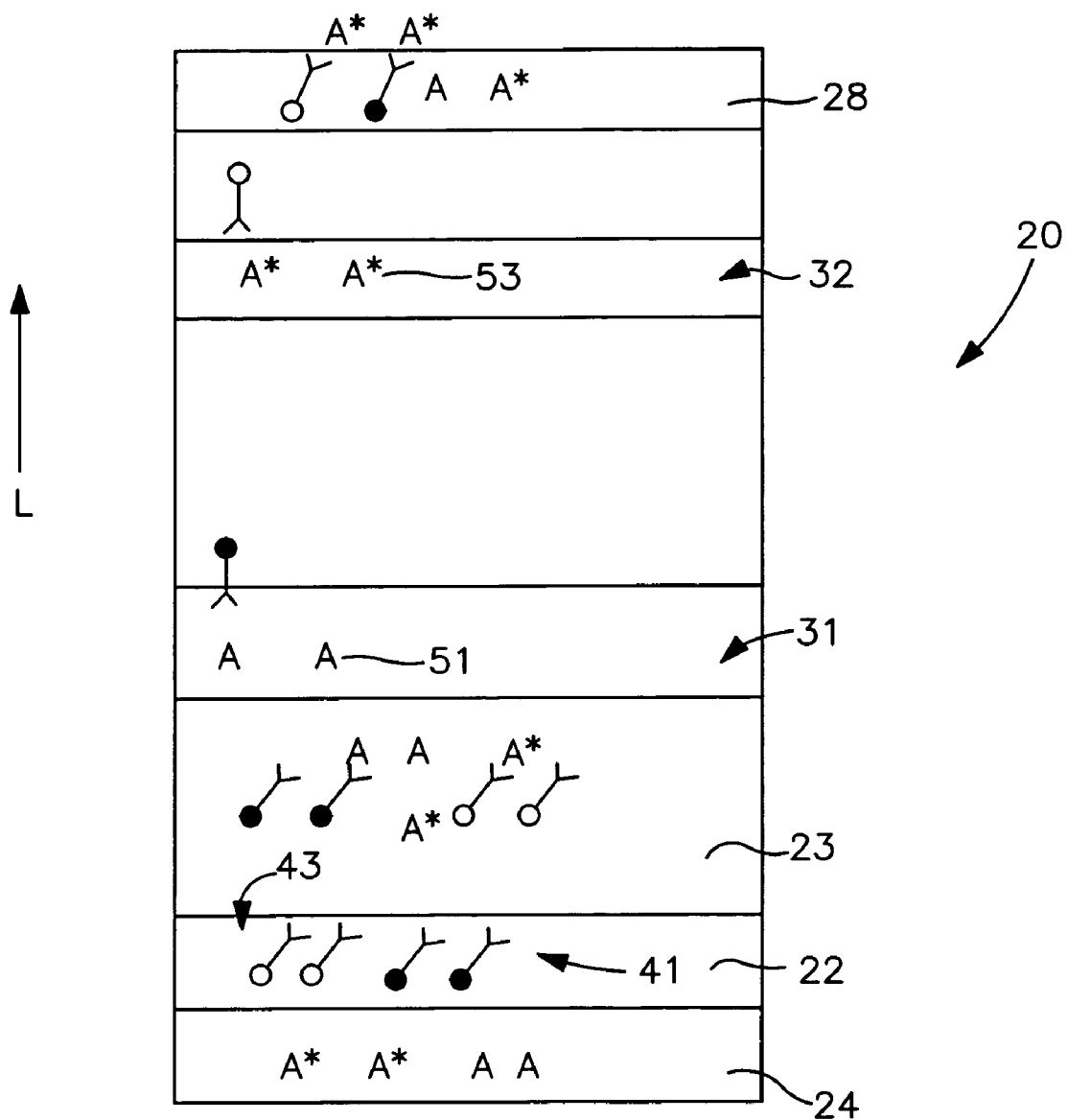
FIG. 3 is a schematic illustration of one embodiment of an indirect assay format that may be used in accordance with the present invention.

Initially, a calibration antigen A* (e.g., PTX3) is pre-applied to the sample pad 24, and conjugated detection probes 41 and conjugated calibration probes 43 are pre-applied to the conjugate pad 22. In one embodiment, for example, the detection probes 41 are dyed particles conjugated with an antibody for CRP (e.g., CRP $IgG_1$) and the calibration probes 43 are dyed particles conjugated with an antibody for PTX3 that does not cross-react with other pentraxin family members (e.g., rat anti-body PTX3 (clone MNB4)). To initiate the assay, a test sample containing the test antigen A is applied to the sample pad 22 where it mixes with the calibration antigen A*. The test antigen A and calibration antigen A* travel in a direction "L" to the conjugate pad 22, where they mix with the detection probes 41 and calibration probes 43. The test antigen A binds with the detection probes 41 to form analyte/probe complexes 49, and the calibration antigen A* binds with the calibration probes 43 to form analyte/probe complexes 50. The complexes 49 and 50 then travel to the detection zone 31, within which is immobilized a first receptive material 51. For example, the first receptive material may be an antibody for CRP that is different than the antibody of the conjugated detection probes (e.g., anti-CRP $IgG_2$) or an antibody for CRP that is identical to the antibody conjugated to the detection probes. The complexes 49 bind to the available binding sites on the immobilized receptive material 51. The remaining complexes 50 then travel to the calibration zone 32, within which is immobilized a second receptive material 53. For example, the second receptive material may be an antibody for PTX3 that is the same or different than the antibody of the conjugated calibration probes (e.g., a different clone of rat anti-body PTX3). The complexes 50 bind to the available binding sites on the immobilized receptive material 53. The intensity of the signals produced by the detection probes 41 captured at the detection zone 31 and the calibration probes 43 at the calibration zone 32 may then be measured. Referring to FIG. 3, another embodiment of a method for detecting the presence of a test antigen A using an indirect assay format will now be described in more detail. In this embodiment, the detection probes 41 are conjugated with an antibody for the test antigen A, and the calibration probes 43 are conjugated with an antibody for the calibration antigen A*. In addition, the first receptive material 51 is similar in nature to the test antigen A, and the second receptive material 53 is similar in nature to the calibration antigen A*. In this manner, the test antigen A and the first receptive material 51 compete for the available binding sites on the conjugated detection probes 41, and the calibration antigen A* and the second receptive material 53 compete for the available binding sites on the conjugated calibration probes 43.

Figure 4:
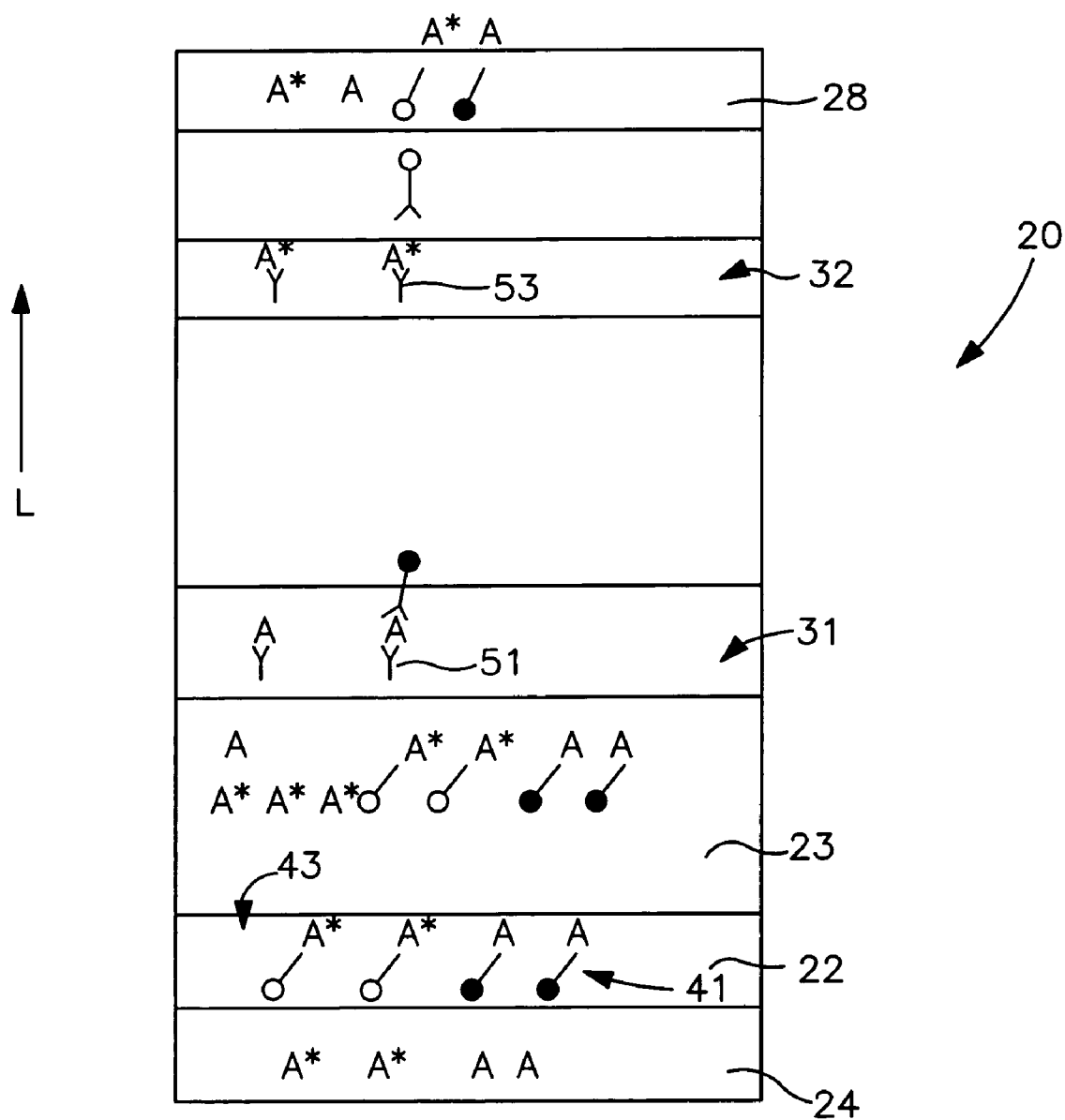
FIG. 4 is a schematic illustration of one embodiment of a competitive assay format that may be used in accordance with the present invention.

Also, referring to FIG. 4, still another embodiment of a method for detecting the presence of a test antigen A using a competitive assay format will now be described in more detail. In this embodiment, the detection probes 41 are conjugated with an antigen that is similar in nature to the test antigen A, and the calibration probes 43 are conjugated with an antigen that is similar in nature to the calibration antigen A*. In addition, the first receptive material 51 is an antibody for the test antigen A, and the second receptive material 53 is an antibody for the calibration antigen A*. In this manner, the test antigen A and the conjugated detection probes 41 compete for the available binding sites on the first receptive material 51, and the calibration antigen A* and the conjugated calibration probes 43 compete for the available binding sites on the second receptive material 53.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

The present invention may be better understood with reference to the following examples.

EXAMPLE 1

The ability to form a lateral flow assay device in accordance with the present invention was demonstrated. A nitrocellulose porous membrane (HF 120 from Millipore, Inc.) having a length of approximately 30 centimeters was laminated onto supporting cards. Monoclonal antibody for C-reactive protein was immobilized on the porous membrane to form a detection zone. The antibody was obtained from BiosPacific, Inc. (Catalog #A58040136P) and had a concentration of 1 milligram per milliliter. Monoclonal antibody for β-HCG (1 milligram per milliliter) was also immobilized on the porous membrane to form a calibration zone. A cellulose wicking pad (Millipore Co.) was laminated with one end (closer to the calibration zone) of the membrane. The membrane samples were then dried for 1 hour at a temperature of 37° C.

A particle suspension was formed by mixing 36 microliters of gold particles conjugated with anti-CRP monoclonal antibody (BiosPacific, Inc., Catalog #A58110228P), 100 microliters of gold particles conjugated with anti α-hCG monoclonal antibody, 500 milliliters of sucrose in water (20%) and 1200 microliters of water. The gold particles conjugated with anti CRP monoclonal antibody had a particle size of 40 nanometers and an optical density of 50.2, and were obtained from British Biocell International. The gold particles conjugated with anti α-hCG monoclonal antibody had a particle size of 40 nanometers and an optical density of 10.1, and were obtained from British Biocell International, Inc. The particle suspension was then loaded onto a 30-centimeter long glass fiber conjugate pad (Millipore Co.). The glass fiber pad was then dried at 37° C. for 2 hours to form a conjugate pad. The conjugate pad was then laminated onto the other end (closer to the detection zone) of the porous membrane. A cellulose wicking pad (Millipore Co.) sample pad was further laminated onto the conjugate pad. The laminated full card was then cut into 4-millimeter wide lateral flow assay devices.

EXAMPLE 2

The ability to detect CRP in accordance with the present invention was demonstrated. Five lateral flow devices (Samples 1-5) were made as described in Example 1. A mixing solution containing 60 microliters of CRP (90 nanograms per milliliter) and 60 microliters of β-hCG (50 nanograms per milliliter) was applied to the sample pad of each of five lateral flow devices. After 30 minutes of development at room temperature, the color density of the detection zone and calibration zone was measured using a reflectance spectrophotometer. The color intensity for each zone is listed below in Table 1.

TABLE 1

Color Intensity Data

| Sample | Detection Zone Intensity ($I_d$) | Detection Zone Intensity ($I_c$) | $I_d/I_c$ |
|---|---|---|---|
| 1 | 88.285 | 95.279 | 0.92659 |
| 2 | 93.554 | 98.322 | 0.95115 |
| 3 | 91.850 | 98.873 | 0.92897 |
| 4 | 94.286 | 101.544 | 0.92852 |
| 5 | 92.580 | 99.990 | 0.92589 |

The mean, standard deviation, and % CV (coefficient of variance, or ratio of standard deviation to mean) for $I_d$ was 92.111, 2.33127, and 2.531, respectively. On the other hand, the mean, standard deviation, and % CV for $I_d/I_c$ was 0.9323, 0.01081, and 1.1159, respectively. Thus, as indicated, the standard deviation and % CV were much lower for the calibrated signal intensity than the uncalibrated signal intensity.

EXAMPLE 3

The ability to detect CRP in accordance with the present invention was demonstrated. Fifteen lateral flow devices (Samples 1-15) were made as described in Example 1 and divided into three groups. The first group was stored at room temperature, the second group was heated at 65° C. for 40 minutes, and the third group was heated at 65° C. for 210 minutes. A mixing solution containing 60 microliters of CRP (100 nanograms per milliliter) and 60 microliters of β-hCG (50 nanograms per milliliter) in tris buffer with 1% Tween® 20 (ICI Americas) was applied to the sample pad of each of fifteen lateral flow devices. After 30 minutes of development at room temperature, the color density of the detection zone and calibration zone was measured using a reflectance spectrophotometer. The color intensities for each group are listed below in Tables 2-4.

TABLE 2

Color Intensity Data for First Group

| Sample | Detection Zone Intensity ($I_d$) | Detection Zone Intensity ($I_c$) | $I_d/I_c$ |
|---|---|---|---|
| 1 | 94.303 | 99.106 | 0.95154 |
| 2 | 93.980 | 97.933 | 0.95964 |
| 3 | 94.719 | 97.618 | 0.97030 |
| 4 | 90.332 | 95.088 | 0.94998 |
| 5 | 93.343 | 96.032 | 0.97200 |

The mean, standard deviation, and % CV for $I_d$ was 93.3354, 1.75261, and 1.878, respectively. On the other hand, the mean, standard deviation, and % CV for $I_d/I_c$ was 0.96069, 0.01024, and 1.066, respectively.

TABLE 3

Color Intensity Data for Second Group

| Sample | Detection Zone Intensity ($I_d$) | Detection Zone Intensity ($I_c$) | $I_d/I_c$ |
|---|---|---|---|
| 1 | 90.9110 | 94.189 | 0.96520 |
| 2 | 90.4130 | 94.266 | 0.95913 |
| 3 | 90.4860 | 93.614 | 0.96659 |
| 4 | 90.4399 | 96.666 | 0.97655 |
| 5 | 85.2780 | 88.978 | 0.95842 |

The mean, standard deviation, and % CV for $I_d$ was 90.2974, 3.25741, and 3.607, respectively. On the other hand, the mean, standard deviation, and % CV for $I_d/I_c$ was 0.96517, 0.00732, and 0.758, respectively.

TABLE 4

Color Intensity Data for Third Group

| Sample | Detection Zone Intensity ($I_d$) | Detection Zone Intensity ($I_c$) | $I_d/I_c$ |
|---|---|---|---|
| 1 | 89.270 | 93.359 | 0.95620 |
| 2 | 87.707 | 91.698 | 0.95968 |
| 3 | 90.181 | 92.496 | 0.97497 |
| 4 | 84.396 | 89.233 | 0.94579 |
| 5 | 87.677 | 91.019 | 0.96328 |

The mean, standard deviation, and % CV for $I_d$ was 87.842, 2.204, and 2.509, respectively. On the other hand, the mean, standard deviation, and % CV for $I_d/I_c$ was 0.95935, 0.01074, and 1.12, respectively.

EXAMPLE 4

The ability to form a lateral flow assay device in accordance with the present invention was demonstrated. A nitrocellulose porous membrane (HF 120 from Millipore, Inc.) having a length of approximately 30 centimeters was laminated onto supporting cards. Monoclonal antibody for C-reactive protein was immobilized on the porous membrane to form a detection zone. The antibody was obtained from BiosPacific, Inc. (Catalog #A58040136P) and had a concentration of 1 milligram per milliliter. Monoclonal antibody for β-HCG (1 milligram per milliliter) was also immobilized on the porous membrane to form a calibration zone. A cellulose wicking pad (Millipore Co.) was laminated with one end (closer to the calibration zone) of the membrane. The membrane samples were then dried for 1 hour at a temperature of 37° C.

A particle suspension was formed by mixing 36 microliters of gold particles conjugated with anti-CRP monoclonal antibody (BiosPacific, Inc., Catalog #A58110228P), 100 microliters of gold particles conjugated with anti α-hCG monoclonal antibody, 500 milliliters of sucrose in water (20%) and 1400 microliters of water. The gold particles conjugated with anti CRP monoclonal antibody had a particle size of 40 nanometers and an optical density of 50.2, and were obtained from British Biocell International. The gold particles conjugated with anti a-hCG monoclonal antibody had a particle size of 40 nanometers and an optical density of 10.1, and were obtained from British Biocell International. The particle suspension was then loaded onto a 30-centimeter long glass fiber conjugate pad (Millipore Co.). The glass fiber pad was then dried at 37° C. for 2 hours to form a conjugate pad. The conjugate pad was then laminated onto the other end (closer to the detection zone) of the porous membrane. A cellulose wicking pad (Millipore Co.) sample pad was further laminated onto the conjugate pad. The laminated full card was then cut into 4-millimeter wide lateral flow assay devices.

EXAMPLE 5

The ability to detect CRP in accordance with the present invention was demonstrated. Fifteen lateral flow devices (Samples 1-15) were made as described in Example 4 and divided into three groups. The first group was stored at room temperature, the second group was heated at 65° C. for 40 minutes, and the third group was heated at 65° C. for 210 minutes. A mixing solution containing 60 microliters of CRP (100 nanograms per milliliter) and 60 microliters of β-hCG (50 nanograms per milliliter) in 20 millimolar Hepes buffer (pH of 7.51) with 1% Tween® 20 (ICI Americas) was applied to the sample pad of the first group. A mixing solution containing 60 microliters of CRP (100 nanograms per milliliter) and 60 microliters of β-hCG (50 nanograms per milliliter) in 20 millimolar Hepes buffer (pH of 8.0) with 1% Tween® 20 (ICI Americas) was applied to the sample pad of the second group. A mixing solution containing 60 microliters of CRP (100 nanograms per milliliter) and 60 microliters of β-hCG (50 nanograms per milliliter) in 20 millimolar Hepes buffer (pH of 8.5) with 1% Tween® 20 (ICI Americas) was applied to the sample pad of the third group.

After 30 minutes of development at room temperature, the color density of the detection zone and calibration zone was measured using a reflectance spectrophotometer. The statistical data for each group are listed below in Table 5.

TABLE 5

| Device | pH | Signal Intensity | Mean | Standard Deviation | % CV |
|---|---|---|---|---|---|
| 1-5 | 7.51 | $I_d$ | 88.720 | 2.885 | 3.252 |
|  |  | $I_d/I_c$ | 1.04440 | 0.00729 | 0.698 |
| 6-10 | 8.00 | $I_d$ | 84.3080 | 1.5491 | 1.837 |
|  |  | $I_d/I_c$ | 1.20340 | 0.00769 | 0.639 |
| 11-15 | 8.50 | $I_d$ | 88.910 | 2.675 | 3.009 |
|  |  | $I_d/I_c$ | 1.04715 | 0.00629 | 0.601 |

As indicated, the calibrated data for the detection zone had a much lower standard deviation and % CV than the non-calibrated data over a range of pH values.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test kit for detecting the presence or quantity of a test analyte within a test sample, the diagnostic test kit comprising:
a lateral flow assay device comprising a porous membrane, the porous membrane defining a detection zone and a calibration zone, wherein a first receptive material is immobilized within the detection zone and a second receptive material is immobilized within the calibration zone;
a plurality of assay reagents, wherein the assay reagents comprise a calibration analyte that is disposed on the lateral flow device, wherein the calibration analyte and the test analyte are members of the same protein family, the assay reagents further comprising detection probes and calibration probes disposed on the lateral flow device prior to the application of a test sample to the device, the detection probes being disposed upstream from the detection zone on the lateral flow device, the calibration probes being disposed upstream from the calibration zone on the lateral flow device, the detection probes being conjugated with a first specific binding member configured to preferentially bind to the test analyte and the calibration probes being conjugated with a second specific binding member configured to preferentially bind to the calibration analyte, further wherein the first receptive material is configured to preferentially bind to the test analyte to form a sandwich complex, and the second receptive material is configured to preferentially bind to the calibration analyte to form a sandwich complex; and
the detection zone being capable of producing a detection signal and the calibration zone being capable of producing a calibration signal, the intensity of the detection signal, as calibrated by the intensity of the calibration signal, being directly proportional to the concentration of the test analyte within the test sample.

2. The diagnostic test kit of claim 1, wherein the detection probes comprise a luminescent compound or a visual label.

3. The diagnostic test kit of claim 1, wherein the first specific binding member, the second specific binding member, the first receptive material, and the second receptive material are immunoreactive binding members.

4. The diagnostic test kit of claim 1, wherein the test analyte is a pentraxin protein.

5. The diagnostic test kit of claim 4, wherein the test analyte is C-reactive protein.

6. The diagnostic test kit of claim 4, wherein the calibration analyte is a pentraxin protein.

7. The diagnostic test kit of claim 6, wherein the calibration analyte is a phosphocholine-binding pentraxin protein.

8. The diagnostic test kit of claim 7, wherein the calibration analyte is pentraxin 3, neuronal pentraxin 1, or neuronal pentraxin 2.

9. The diagnostic test kit of claim 1, wherein the calibration zone is located downstream from the detection zone.

10. The diagnostic test kit of claim 1, wherein the lateral flow assay device further comprises a conjugate pad in fluid communication with the porous membrane, wherein one or more of the assay reagents are disposed on the conjugate pad.

11. The diagnostic test kit of claim 10, wherein the detection probes and calibration probes are disposed on the conjugate pad.

12. The diagnostic test kit of claim 10, further comprising a sample pad that is positioned upstream from the conjugate pad and defines a point of application for the test sample, wherein the calibration analyte is disposed on the sample pad.

13. The diagnostic test kit of claim 1, wherein one or more of the assay reagents are disposed on the lateral flow device at a location that is downstream from a point of application for the test sample.

14. The diagnostic test kit of claim 1, wherein one or more of the assay reagents are disposed on the lateral flow device at a location that is upstream from a point of application for the test sample.

15. A diagnostic test kit for detecting the presence or quantity of a test analyte within a test sample, the diagnostic test kit comprising:
a lateral flow assay device comprising a porous membrane, the porous membrane defining a detection zone and a calibration zone, wherein a first receptive material is immobilized within the detection zone and a second receptive material is immobilized within the calibration zone;
a calibration analyte disposed on the lateral flow assay device at a first area, wherein the calibration analyte and the test analyte are members of the same protein family;
detection probes disposed on the lateral flow assay device, the detection probes being disposed upstream from the detection zone on the lateral flow device, the detection probes being conjugated with a first specific binding member configured to preferentially bind to the test analyte; and calibration probes disposed on the lateral flow assay device at a second area prior to the application of a test sample to the device, the calibration probes being disposed upstream from the calibration zone on the lateral flow device, the calibration probes being conjugated with a second specific binding member configured to preferentially bind to the calibration analyte, further wherein the first receptive material is configured to preferentially bind to the test analyte to form a sandwich complex, and the second receptive material is configured to preferentially bind to the calibration analyte to form a sandwich complex; and the detection zone being capable of producing a detection signal and the calibration zone being capable of producing a calibration signal, the intensity of the detection signal, as calibrated by the intensity of the calibration signal, being directly proportional to the concentration of the test analyte within the test sample.

16. The diagnostic test kit of claim 15, wherein the detection probes comprise a luminescent compound or a visual label.

17. The diagnostic test kit of claim 15, wherein the first specific binding member, the second specific binding member, the first receptive material, and the second receptive material are immunoreactive binding members.

18. The diagnostic test kit of claim 15, wherein the test analyte is a pentraxin protein.

19. The diagnostic test kit of claim 18, wherein the calibration analyte is a pentraxin protein.

20. The diagnostic test kit of claim 15, wherein the calibration zone is located downstream from the detection zone.

21. The diagnostic test kit of claim 15, wherein the first area is upstream of the second area.

22. The diagnostic test kit of claim 15, wherein the detection probes are disposed in the second area.

23. The diagnostic test kit of claim 15, wherein the first area is a sample pad and the second area is a conjugate pad.

* * * * *